(12) United States Patent
Pazos Pérez et al.

(10) Patent No.: US 10,150,160 B2
(45) Date of Patent: Dec. 11, 2018

(54) UNIVERSAL ONE-POT AND UP-SCALABLE SYNTHESIS OF SERS ENCODED NANOPARTICLES

(71) Applicant: Medcom Advance, S.A, Barcelona (ES)

(72) Inventors: Nicolás Pazos Pérez, Barcelona (ES); Bernat Mir De Simón, Barcelona (ES)

(73) Assignee: Medcom Advance, S.A., Barcelona (ES)

(*) Notice: Subject to any disclaimer, the term of this patent is extended or adjusted under 35 U.S.C. 154(b) by 44 days.

(21) Appl. No.: 15/533,093

(22) PCT Filed: Dec. 4, 2014

(86) PCT No.: PCT/EP2014/076627
§ 371 (c)(1),
(2) Date: Jun. 5, 2017

(87) PCT Pub. No.: WO2016/086999
PCT Pub. Date: Jun. 9, 2016

(65) Prior Publication Data
US 2017/0326638 A1    Nov. 16, 2017

(51) Int. Cl.
*G01N 21/65* (2006.01)
*B22F 1/00* (2006.01)
*B22F 9/24* (2006.01)

(52) U.S. Cl.
CPC .......... *B22F 1/0022* (2013.01); *B22F 1/0018* (2013.01); *B22F 1/0062* (2013.01); *B22F 9/24* (2013.01); *G01N 21/658* (2013.01); *B22F 1/00* (2013.01)

(58) Field of Classification Search
CPC ............. G01N 21/65; G01N 33/54346; G01N 21/658; G01N 33/587
USPC ................................................... 436/164, 166
See application file for complete search history.

(56) References Cited

U.S. PATENT DOCUMENTS 9,327,314 B2 *   5/2016   Zhong ..................... B01J 13/02

* cited by examiner

*Primary Examiner* — Gregory E Webb

(57) ABSTRACT

The universal one-pot and up-scalable synthesis of SERS encoded nanoparticles relies on the controlled co-absorption of mercaptoundecanoic acid (MUA) and the Raman code on the metallic surfaces of the nanoparticles. In contrast to most of the reported procedures which typically involve complex steps, the present method has demonstrated to be an easy and fast one-pot approach for the production of SERS-encoded nanoparticles. This versatile strategy allows for the SERS codification of particles with every molecule with affinity toward the metal surface, independently of its chemical nature, as exemplified here in the fabrication of 31 different encoded particles using the same standard procedure. In addition to the easiness of preparation, scalability to the liter regime, stability in aqueous solutions including PBS and chemical diversity, our SERS-encoded particles show considerably higher optical efficiency than those fabricated by using PEG or PVP polymers.

12 Claims, 8 Drawing Sheets

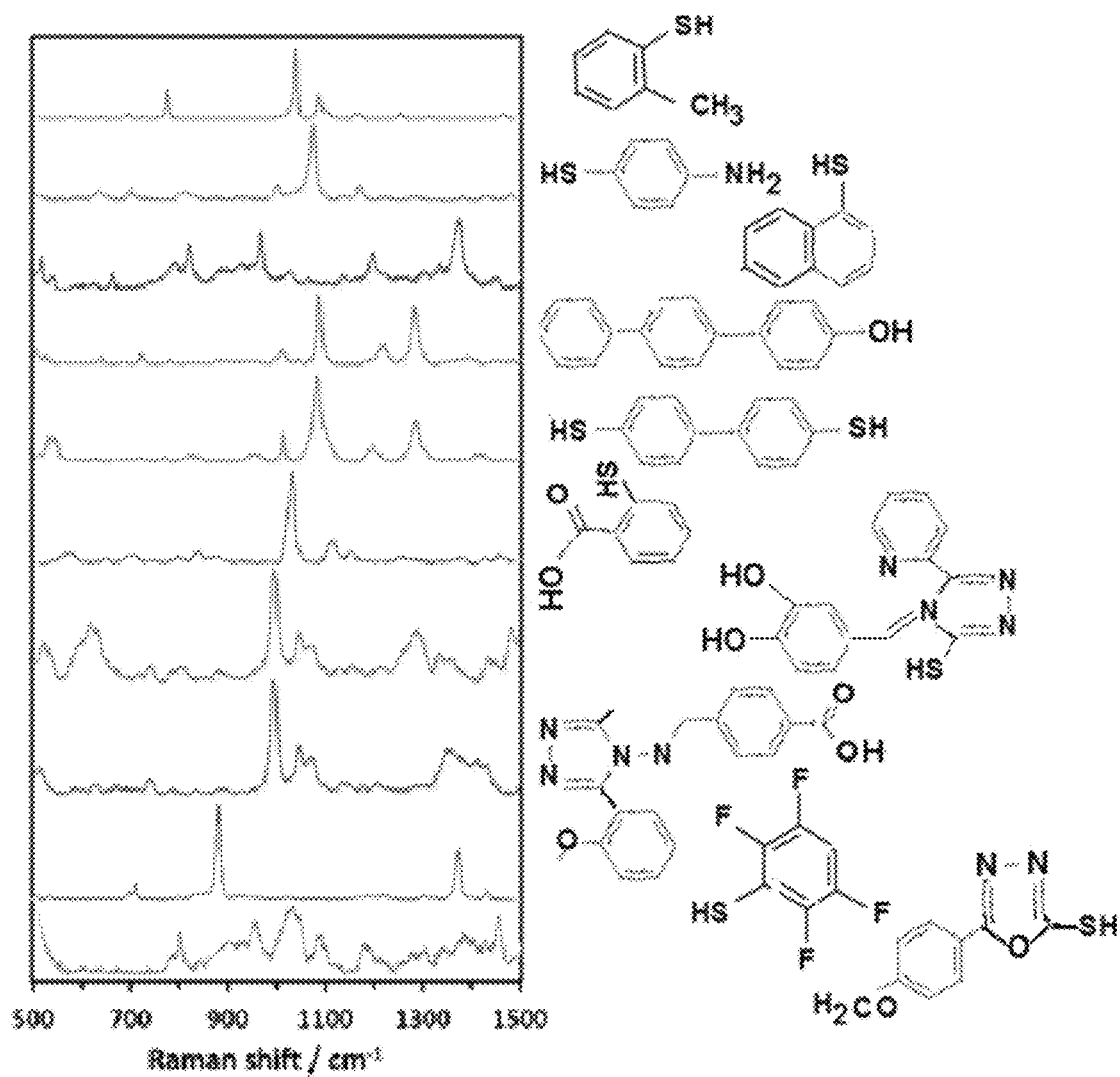
Figure 10 (continuation)

Nile blue A     2,3,4,6 Tetrafluorobenzenethiol     Toluidine blue

UNIVERSAL ONE-POT AND UP-SCALABLE SYNTHESIS OF SERS ENCODED NANOPARTICLES

RELATED APPLICATION

This application is a National Phase of PCT Patent Application No. PCT/EP2014/076627, having International filing date of Dec. 4, 2014, the contents of which are all incorporated by reference as if fully set forth herein in their entirety.

FIELD AND BACKGROUND OF THE INVENTION

The present invention relates to a method for synthesizing SERS (Surface-Enhanced Raman Scattering) encoded nanoparticles. These particles are useful in different fields such as high-throughput multiplex screening[1] in microarray technology,[2] diagnosis[3] and bioimaging.[4]

Encoded nanoparticles are between the most powerful alternatives for high-throughput multiplex screening[1] in microarray technology,[2] diagnosis[3] and bioimaging.[4] These materials are simple and cost-effective platforms which allow for fast, sensitive and reliable analysis.[1b, 5] During the last decade, several encoded particles were prepared[6] using codification strategies based on changes in particle shape,[7] composition,[8] physical marks[6c] or spectroscopic properties (e.g. luminescence or vibrational fingerprints).[4, 9] Among all of them, those based on Surface-Enhanced Raman Scattering (SERS) are gaining importance [10] due to: i) the virtually unlimited multiplexing capability associated with the unique vibrational fingerprint of the different codes, ii) short detection times (milliseconds) thanks to the intrinsic sensitivity of the SERS phenomena; [11] iii) small size, allowing for bioimaging;[12] and, iv) photostability and low toxicity (as compared with those of dyes or quantum dots).[13]

In essence, a SERS-encoded nanoparticle (also indicated as SERS-tag) comprises a plasmonic nucleus, responsible for the generation of the electric field necessary for the Raman amplification; a Raman probe (i.e. code), responsible of the unique vibrational fingerprint of the encoded particle; and, a coating layer. This external coating is of key importance as: i) prevents the code from leaching out into the medium thus avoiding toxic effects or vibrational cross-contamination with the codes of other particles; ii) protects the plasmonic particle from contaminations of the medium that may give rise to vibrational noise hindering the particle readout; iii) increases the colloidal stability of the particle; iv) provides a convenient surface for further chemical functionalization; and, v) protects the plasmonic core for interacting with other plasmonic particles avoiding plasmon coupling and so the uncontrolled generation of hotspots. Although, polymers, have been reported as particles coatings[12b, 14] the unique properties of silica (i.e. known surface chemistry, biocompatibility, optical transparency and colloidal stability) make this material the most efficient protective layer for nanoparticles by far.[15] US2006054506A1 discloses a method for synthesizing encapsulated SERS encoded nanoparticles in which a selected SERS encoding molecule is added to an aqueous suspension of metal nanoparticles, and after that, the SERS encoding nanoparticles are encapsulated in a silica matrix. However, this procedure is restricted only to a limited number of encoding molecules, those containing already pyridyl or silane groups, because these groups can act as silica precursors.

Silica coating of nanoparticles requires the colloidal stabilization of the particles in ethanolic solution prior to the hydrolysis/condensation of tetraethyl orthosilicate (TEOS). Though a range of polymers have been described for this task,[15a, 16] the most common remains polyvinylpyrrolidone (PVP).[15a, 16] On the other hand, surfactants such as cetyl-trimethyl ammonium bromide (CTAB) also are used commonly for this reaction.[15a] Notwithstanding, the fact that the most important factor for the generation of active SERS-encoded particles relies in the intimate contact between the Raman code and the plasmonic particle, introduces further complexity to the coating process associated with the surface chemistry properties. Both PVP and CTAB form solid layers of coating on the surface of the particles limiting or even avoiding the interaction of the encoding agent with the metallic surface when added to the solution. [17] Therefore, to increase the code adsorption efficiency on the plasmonic structure, and thus the SERS signal, PVP and CTAB species need to be removed from the metallic surfaces. On the other hand, this usually results in a drastic reduction of the colloidal stability, which is further aggravated by the non-polar nature of most of the codes, leading to uncontrolled particle agglomeration[11, 18] or even to irreversible precipitation. Aggregation of labelled-nanoparticles into clusters of different size and geometry does generate very active SERS structures but with highly inhomogeneous SERS response. Moreover, these fabrication methods normally work for a very limited number of encoding molecules as, in many cases, precipitation of the whole colloids occurs upon addition of the code. In fact, this explains why in most of the literature, examples of SERS encoded particles include a small number of codes, usually just three or four.

As an alternative to the conventional polymers or surfactants, thiolated poly(ethylene glycol) (PEG) had been successfully employed for the controlled silica coating of single metallic nanoparticles. The high polarity and porosity of this polymer efficiently stabilize particles in alcohol and water while allow for the diffusion of the code to the metallic surface.[19] No matter, as commonly in polymers, PEG size distribution normally suffers from large fluctuations from batch-to-batch, even for the same commercial brand. As a result, the synthetic protocol to encode particles using this method needs to be tuned every time a new PEG is purchased. Additionally, the high price of the thiolated-PEG hinders its use to the large-scale preparation of encoded particles as required for real life applications.

SUMMARY OF THE INVENTION

Consequently, the problem to be solved by the skilled person is to provide an alternative method for synthesizing SERS encoded nanoparticles that overcomes the disadvantages of the methods of the prior art. The solution is based on a method that relies on the controlled co-absorption of mercaptoundecanoic acid (MUA) and the Raman code on the metallic surfaces. MUA binds to the particle surface through the thiol group while provides steric and electrostatic particle stability because of its aliphatic chain and the final carboxylic group. On the other hand, due to its aliphatic nature, its SERS cross section is almost negligible as compared with those of the Raman codes. This process allows the use of a very big library of Raman codes because, using a very small amount of MUA it is possible to stabilize the particles meanwhile leaving a lot of free surface for the Raman code. Moreover, because of its final carboxylic group, it is able to act as precursor for the silica growth.

Accordingly, a first aspect of the invention is directed to a method for synthesizing encapsulated SERS encoded nanoparticles comprising the following steps:
  a) providing an aqueous suspension of metal nanoparticles;
  b) adding aliphatic thiols with carboxylic groups to the suspension to yield stabilized nanoparticles;
  c) adding a selected SERS encoding molecule to the suspension; and
  d) encapsulating the SERS encoded nanoparticles in a silica matrix.

In a preferred form, is a method for synthesizing encapsulated SERS encoded nanoparticles comprising the following steps:
  a) providing an aqueous colloidal suspension of metal nanoparticles;
  b) adding mercaptoundecanoic acid (MUA) to the suspension to yield MUA-stabilized nanoparticles;
  c) adding a selected SERS encoding molecule to the suspension; and
  d) encapsulating the SERS encoded nanoparticles in a silica matrix.

In contrast to most of the reported procedures which typically involve complex steps, herein we demonstrate an easy and fast one-pot approach for the production of SERS-encoded nanoparticles. This versatile strategy allows for the SERS codification of particles with every molecule with affinity toward the metal surface, independently of its chemical nature, as exemplified here in the fabrication of 31 different encoded particles using exactly the same standard procedure. In addition to the easiness of preparation, scalability to the liter regime, stability in aqueous solutions including PBS and chemical diversity, our SERS-encoded particles show considerably higher optical efficiency than those fabricated by using PEG or PVP polymers.

In a second aspect, the suspension of metal nanoparticles is a suspension of nanoparticles of gold, silver, copper, aluminum, their alloys with themselves or their alloys with others.

In a third aspect, the step b) of the method of invention is carried out by adding a solution containing $NH_4OH$ and MUA rapidly and under vigorous stirring to the suspension of metal nanoparticles.

In a fourth aspect, the step c) of the method of invention is carried out by adding a solution containing EtOH and $NH_4OH$ to the suspension of MUA-stabilized nanoparticles and then adding thereto a solution containing the selected SERS encoding molecule.

In a fifth aspect, the step c) of the method of invention is carried out is carried out by adding a solution containing EtOH and $NH_4OH$ to the suspension of MUA-stabilized nanoparticles and then adding thereto a solution containing the selected SERS encoding molecule. Preferably, the solution containing the SERS encoding molecule is added to the suspension of MUA-stabilized nanoparticles under strong magnetic stirring and in a large excess of molecules per $nm^2$ with respect to the MUA-stabilized nanoparticles.

Other aspect of the invention is that nanoparticles are formed by a suspension of citrate-capped spherical gold nanoparticles that is produced by adding an aqueous solution of $HAuCl_4$ into a boiling aqueous solution of sodium citrate under vigorous stirring, and then maintaining the heating and stirring at appropriate levels until the solvent is at least partially evaporated.

According to other aspect, the SERS encoding molecule is selected from molecules that have a functional group with high affinity to the metal surfaces as thiols, amines or cyanides. Preferably, the SERS encoding molecule is selected from the group consisting of: 2-mercaptopyridine; benzenethiol; mercaptobenzoic acid; 4-nitrobenzenethiol; 3,4-dicholorobenzenethiol, 3-fluorothiophenol; 4-fluorothiophenol; 3-5-bis(trifluoromethyl)benzenethiol; methylene blue; nile blue A; rhodamine 6G; Toluidine Blue O, 2-Phenylethanethiol, 4-Mercaptophenol, Biphenyl-4-thiol, 7-Mercapto-4-methylcoumarin, 4-Hydroxyphenyl)-1H-tetrazole-5-thiol, 2-Fluorothiophenol, Crystal Violet, 2-Naphthalenethiol, 4-(((3-Mercapto-5-(2-methoxyphenyl)-4H-1,2,4-triazol-4-yl)imino)methyl)phenol, (2-Trifluoromethyl)benzenethiol, 4-Aminothiophenol, 1-Naphthalenethiol, 1,1',4,1''-Terphenyl-4-Thiol, Biphenyl-4,4'-dithiol, Thiosalicylic acid, 4-(((3-Mercapto-5-(2-pyridinyl)-4H-1,2,4-triazol-4-yl)imino)methyl)-1,2-benzenediol, 4-(((3-Mercapto-5-(2-pyridinyl)-4H-1,2,4-triazol-4-yl)imino)methyl) benzoic, 2,3,4,6-Tetrafluorobenzenethiol, and (5-(4-Methoxyphenyl)-1,3,4-oxidazole-2-thiol).

According to other aspect, the encapsulation of the SERS encoded nanoparticles in a silica matrix is carried out by adding to the dispersion of SERS encoded nanoparticles appropriate amounts of ethanol and NH4OH to provide an EtOH/H2O molar ratio between 0.2 and 5, and then adding tetraethyl orthosilicate to initiate the silica growth. Preferably, the solution is thereafter allowed to react between 1 h and 24 h at room temperature and then submitted to several washing cycles.

According to other aspect the method of invention is scalable to the liter regime.

EXAMPLES

Figure 1:
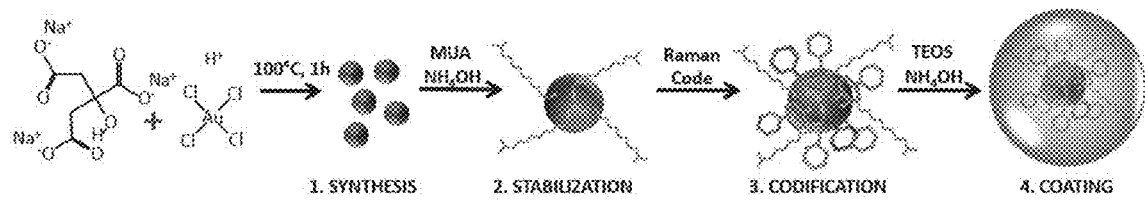
FIG. 1: Schematic representation of the synthetic procedure for the production of SERS-encoded nanoparticles showing the different steps involved in the synthesis. First, citrate capped Au nanoparticles are produced. Second, MUA is used to stabilize the particles in basic media. Third, an excess of SERS code is added to encode the particles. Fourth, a silica shell is growth on the particles to ensure stability for long periods of time and avoid undesired plasmon coupling.

The following examples illustrate the invention and should not be considered as defining the full scope thereof.

The following materials and methods are used for the examples of invention: Gold(III) chloride trihydrate (99.9%, HAuCl4.3H$_2$O), trisodium citrate dehydrated (≥99.5%, C$_6$H$_5$Na$_3$O$_7$.2H$_2$O), ammonia solution (29%, NH$_4$OH), tetraethoxy silane (99.999%, TEOS), ethanol (99.5%, EtOH), polyvinylpyrrolidone (average M.W. 58.000 g, PVP), cetyltrimethylammonium bromide (99.72%, CTAB), 11-mercapto undecanoic acid (95%, MUA), 2-mercaptopyridine (97%, MPy), 4-nitrobenzenethiol (80%, 4NBT), 4-mercaptophenol (97%, 4MP), 4-mercaptobenzoic acid (99%, MBA), 3,5-bis(trifluoromethyl) benzenethiol (97%, 35BTFMB), 4-fluorothiophenol (98%, 4FTP), 2,3,5,6-tetrafluoro benzenethiol (97%, 2346TFBT), 2-(trifluoromethyl)benzenethiol (96%, 2TFMBT), 3-fluorothiophenol (95%, 3FTP), nile blue A (95%, NBA), 2-fluorothiophenol (97%, 2FTP), toluidine blue O (≥84%, TB), benzenethiol (97%, BT), 4-(((3-mercapto-5-(2-methoxyphenyl)-4H-1,2,4-triazol-4-yl)imino)methyl)phenol (97%, MMPHTYIMP), 4-(((3-mercapto-5-(2-pyridinyl)-4H-1,2,4-triazol-4-yl)imino)methyl)benzoic acid (MPHTYIMBA), 4-(((3-mercapto-5-(2-pyridinyl)-4H-1,2,4-triazol-4-yl)imino)methyl)-1,2-benzenediol acid (MPHTYIMBDO), 1-(4-hydroxyphenyl)-1H-tetrazole-5-thiol (97%, HPHTT), 1,1',4',1"-terphenyl-4-thiol (97%, TPT), 1-naphtalenethiol (99%, 1NT), 2-naphtalenethiol (99%, 2NT), 5-(4-methoxyphenyl)-1,3,4-oxidazole-2-thiol (97%, MPOT), methylene blue (≥82%, MB), 3,4-dichlorobenzenethiol (97%, DCBT), biphenyl-4-thiol (97%, BPT), 7-mercapto-4-methylcoumarin (≥97%, MMC), biphenyl-4-4'-dithiol (95%, BPDT), thiosalicylic acid (97%, TSA), 5-amino-1,3,4-thiadiazole-2-thiol (87%, ATT), 4-aminothiophenol (97%, 4ATP), 2-phenylethanethiol (98%, 2PET), crystal violet (≥90%, CV) were purchased from Sigma-Aldrich (Germany). All reactants were used without further purification. Mili-Q water (18 MΩ cm$^{-1}$) was used in all aqueous solutions, and all the glassware was cleaned with aqua regia before the experiments.

Example 1

Synthesis of Citrate-Stabilized Spherical Gold Nanoparticles:

Spherical gold nanoparticles of approx. 50 nm in diameter were produced by a modification of the Turkevich method. Briefly, 308 μl aqueous solution of HAuCl$_4$ (0.081 M) were added in to a boiling aqueous solution of sodium citrate (100 mL, 0.27 mM) under vigorous stirring. Heating and stirring were continued for 30 min. A condenser was utilized in order to prevent the evaporation of the solvent. During this time, the colour of the solution gradually changes from colourless to purple to finally become deep red. After this time, heating was continued and the condenser removed in order to allow the evaporation of the solvent to the half of its initial volume, to achieve a final [Au]=5×10$^{-4}$ M.

Example 2

Mercapto Undecanoic Acid Functionalization of Spherical Gold Nanoparticles:

In order to provide colloidal stability to the au nanoparticles during the encoding process and to later on promote the silica growing, 50 mL of the as produced spherical gold nanoparticles were functionalized with a small amount of MUA (0.8 molecules nm$^{-2}$). To this end, a solution containing NH$_4$OH (879 μl, 29% aqueous solution) and MUA (1 mL, 3.99 10$^{-5}$ M in EtOH) was prepared. This solution was then rapidly added under vigorous stirring to the gold nanoparticles sol (50 mL). Agitation was continued for 30 min to assure MUA functionalization on the Au surface.

Example 3

Gold Nanoparticles Codification:
With the aim to prove the versatility of the presented method, 31 different SERS active molecules were used MPy, 4NBT, 4MP, MBA, 35BTFMB, 4FTP, 2356TFBT, 2TFMBT, 3FTP, NBA, 2FTP, TB, BT, MMPHTYIMP, HPHTT, TPT, 1NT, 2NT, MPOT, MB, DCBT, BPT, MMC, BPDT, CV, 2PET, 4ATP, ATT, TSA, MPHTYIMBDO, MPHTYIMBA. The exact same procedure was used for each molecule. Briefly, a solution containing EtOH (324.89 mL) and $NH_4OH$ (5.73 mL, 29% aqueous solution) was prepared. This solution was then rapidly added under vigorous stirring to the MUA stabilized gold nanoparticles (51.88 mL). Next, a stock solution of the SERS active molecule was prepared ($10^{-2}$ M, in EtOH) and 74.8 µl of this solution was added to the Au MUA functionalized particles (382 mL) under strong magnetic stirring for 30 min (to assure proper Au functionalization). The amount added of SERS active molecules was calculated to be 15 molecules $nm^{-2}$.

Example 4

Silica Encapsulation:

The silica encapsulation of the encoded nanoparticles was achieved through a modified-Stöber method using the MUA carboxylic group to promote the silica growth as follows: The proper concentrations of $H_2O$, $NH_4OH$ and EtOH for the silica growth of the MUA-SERS code encoded particles solution was previously adjusted, during the codification step, to yield final concentrations of 7.94 M, 0.128 M and 14.60M, respectively (the molar ratio $EtOH/H_2O=1.84$). Then, TEOS (13.20 µl) was added, the solution was energetically shaken and left undisturbed at room temperature 14 h. Finally, The resulting core-shell NPs were cleaned to remove excess of reactants by centrifugation (3×6000 rpm, 20 min), and redispersed in ethanol. In order to concentrate the solution ($10^{-3}$ M) to perform the SERS characterization, 15.29 mL of this solution were centrifuged again (2×6000 rpm, 20 min) and redispersed in water, after the final centrifugation step everything was resuspended in a final volume of 1 mL.

Example 5

Synthesis of PVP Based Spherical Encoded Gold Nanoparticles:

Different SERS active molecules were used 1NT, MPy, 4NBT, MBA, NBA, TB and 2356TFBT. Spherical gold nanoparticles of approx. 51 nm in diameter were produced as previously described. To 75 mL of PVP solution (0.69 mM), 50 mL of the citrate Au particles were added dropwise and left to react overnight under stirring. Next, the solution was centrifuged (5400 rpm, 25 min) and redispersed in 50 mL EtOH ([Au]=0.5 mM), to remove at maximum the excess of PVP, this process was repeated four times. Then, the SERS code molecule (74.8 µl; $10^{-2}$ M) was added under stirring for 2 h. Finally, silica coating was carried out through adjustment of the final concentrations as follows (in a 50 mL solution): [Au]=0.5 mM, [H2O]=10.55 M, $[NH_3]$=0.2 M, [EtOH]=13.39 M and [TEOS]=1.12 mM. The reaction mixture was allowed to react for 24 h. When reaction time was completed, the particles were centrifuged and washed with ethanol. In order to concentrate the solution ($10^{-3}$ M) to perform the SERS measurements, 2 mL of this solution were centrifuged again (2×6000 rpm, 20 min) and redispersed in water, after the final centrifugation step everything was resuspended in a final volume of 1 mL.

Example 6

Synthesis of PEG-SH Based Spherical Encoded Gold Nanoparticles:

Different SERS active molecules were used 1NT, MPy, 4NBT, MBA, NBA, TB and 2356TFBT. First, CTAB-stabilized gold nanospheres of 51 nm in diameter were prepared by seeded growth approach previously described in the literature[30] as follows: A seed solution was done by preparing an aqueous solution (20 mL) containing $HAuCl_4$ ($2.5 \times 10^{-4}$ M) and sodium citrate ($2.5 \times 10^{-4}$ M). While the mixture was vigorously stirred, $NaBH_4$ (600 µL, 0.1 M) solution was added, observing a fast color change into red which indicates the formation of the gold particles. The seeds were left under stirring at open atmosphere for 1 h to allow the $NaBH_4$ to decompose. Next, a growth solution was prepared by dissolving CTAB (from Mercks, 100 mL, 0.1 M) and potassium iodide (0.3 mg/gram of CTAB) in Milli-Q water followed by the addition of $HAuCl_4$ (510 µL, 0.103 M) and ascorbic acid (735 µL, 0.1 M). After each addition, the bottles were vigorously shaken. 187 µL of seeds were added, and the solution was again vigorously shaken. The flask was left undisturbed at 28° C. during 48 h. After this time, a small amount of gold particles is observed as sediment in the bottom of the flask. Since particles below 100 nm are stable in solution, this precipitate must be composed of larger Au structures coming from seeds with a different crystallographic structure. Carefully, the supernatant is collected and the precipitate discarded in order to ensure the monodispersity of the particles. The second step involves the O-[2-(3mercaptopropionylamino)ethyl]-O0-methylpoly(ethylene glycol) (PEG-SH, Mw 5000) capping, ethanol transfer, and silica coating. To do this, 100 mL of the as-synthesized Au spheres ([Au]=0.25 mM, [CTAB]=0.1 M) were centrifuged for 20 min (6000 rpm), the precipitate was redispersed with a CTAB solution ([CTAB]=0.5 mM) in order to clean at much as possible the CTAB without compromising the colloidal stability of the particles. This process was repeated 3 times to finally redispers in a final volume of 50 mL to obtain [CTAB] ~0.5 mM and [Au] ~0.5 mM. Next, a stock solution of the PEG-SH was prepared and sonicated for 15 min ($10^{-3}$ M, in $H_2O$), 89.8 µl of this solution was added to the Au CTAB stabilized particles (50 mL) under strong magnetic stirring for 30 min (to assure proper Au functionalization). The amount added of PEG-SH was calculated to be 1.8 molecules $nm^{-2}$. The PEG-modified particles were centrifuged twice to remove excess PEG-SH and redispersed in ethanol (50 mL), in the second centrifugation the particles were redispersed in a solution (50 mL) adjusting the following final concentrations: [Au]=0.5 mM, [H2O]=10.55 M, $[NH_3]$=0.2 M and [EtOH]=13.39 M. The third step is the encoding of the nanoparticles, a stock solution of the SERS active molecule was prepared ($10^{-2}$ M, in EtOH) and 74.8 µl of this solution was added to the Au PEG-SH functionalized particles (50 mL) under strong magnetic stirring for 2 h. The amount added of SERS active molecules was calculated to be 15 molecules $nm^{-2}$. Finally, TEOS (13.20 µl) was added, the solution was energetically shaken and left undisturbed at room temperature 14 h. In order to concentrate the solution ($10^{-3}$ M) to perform the SERS measurements, 2 mL of this solution were centrifuged again (2×6000 rpm, 20 min) and redispersed in water, after the final centrifugation step everything was resuspended in a final volume of 1 mL.

Example 7

Characterization:

UV-VIS spectroscopy (PerkinElmer, Lambda 19) and transmission electron microscopy (TEM, LEO 922 EFTEM operating at 80 kV) were applied to characterize the optical response, structure and size of the nanoparticles during the encoding process. SERS spectra were collected in backscattering geometry with a Renishaw Invia Reflex system equipped with a 2D-CCD detector and a Leica confocal microscope. The spectrograph used a high resolution grating (1200 g cm$^{-1}$) with additional band pass filter optics. Excitation of the sample was carried out with a 785 nm diode laser line, with acquisition times of 10$^{-1}$ s (depending on Raman Intensity saturation) and power at the sample of about 300 mW, using the Renishaw's StreamLine accessory. The laser was focused onto the sample with a 30× objective providing a spatial resolution of ca. 1 µm.

Results and Discussion of Examples

Figure 6:
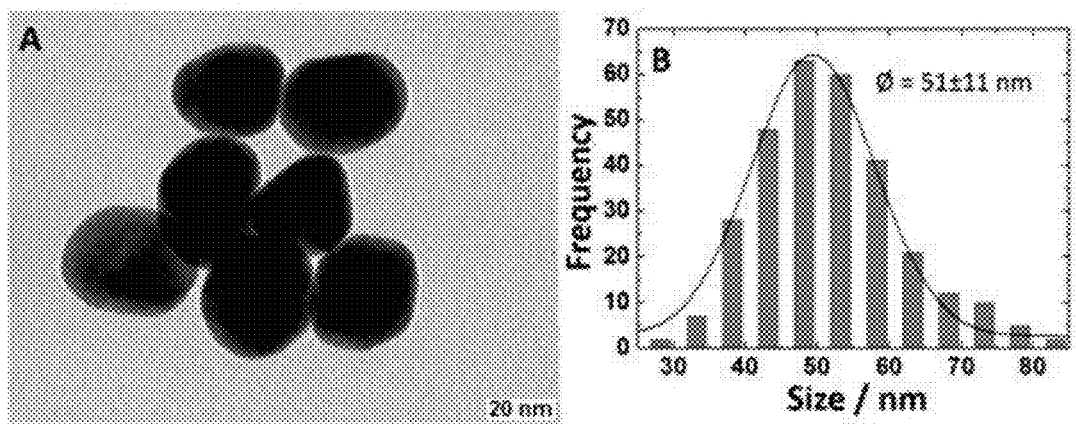
FIG. 6: Representative TEM image (A) and size distribution histograms (B) of the synthesized citrate-capped gold nanoparticles.
Figure 7:
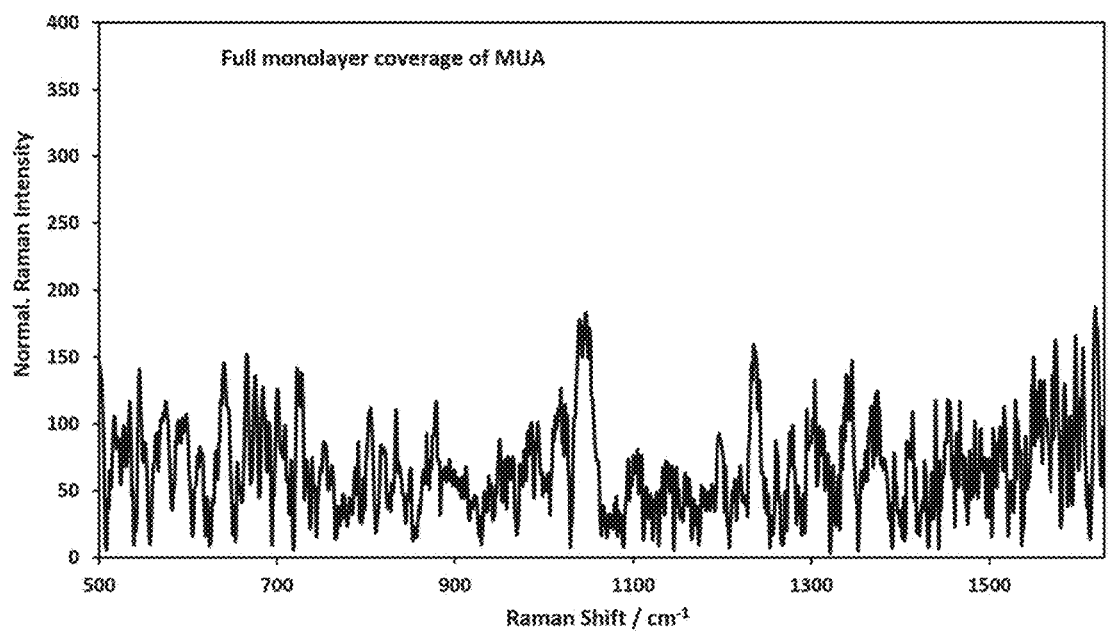
FIG. 7: SERS spectra of Au particles coated with a full monolayer of MUA showing its small Raman cross section.

The schematic outline of the universal protocol for the fabrication of encoded particles is illustrated in FIG. 1. The process can be divided in four different steps; 1) Synthesis of nanoparticles; 2) MUA functionalization; 3) SERS codification; and, 4) Silica coating. As initial plasmonic material, citrate-capped gold nanoparticles of ca. 50 nm diameter (see FIG. 6) were selected as most of the published research in SERS encoded particles is carried out on spherical gold nanoparticles. However, the protocol can be extended to other geometries and materials (i.e. silver). Due to the low stability of colloidal solutions upon functionalization with the Raman code, a stabilization step is required prior to the codification. MUA was chosen as stabilizing agent because binds covalently to the gold surface through the thiol group while provides particle stability with both the long aliphatic chain (steric) and the final carboxylic group (electrostatic). On the other hand, due to its aliphatic nature, its SERS cross section is almost negligible as compared with those of aromatic compounds (FIG. 7).[20] Notwithstanding the presence of a thiol group implies that MUA should be added in the adequate proportion to avoid the formation of a compact monolayer that may passivate the metallic surface preventing the retention of the SERS codes and with extreme care to avoid heterogeneous adsorption of the molecule by some of the colloids of the solution. Thus, in a second step, MUA was rapidly added under vigorous stirring at basic pH to yield MUA functionalized gold nanoparticles (Au@MUA). In order to maximize the final SERS efficiency of the encoded NPs, the MUA surface coverage was decreased as much as possible to provide maximum accessibility to the metal surface while preserving the overall colloidal stability when exposed to an excess of the SERS code. The addition of the code is depicted as the third step (FIG. 1). Among all the investigated encoding molecules, 2-mercaptopyridine (MPy) was observed to induce the fastest colloidal aggregation upon addition to the bare citrate-capped gold nanoparticles. For this reason, the optimization of the protocol was performed by using this molecule (i.e. the worst colloidal stability scenario).

Figure 2:
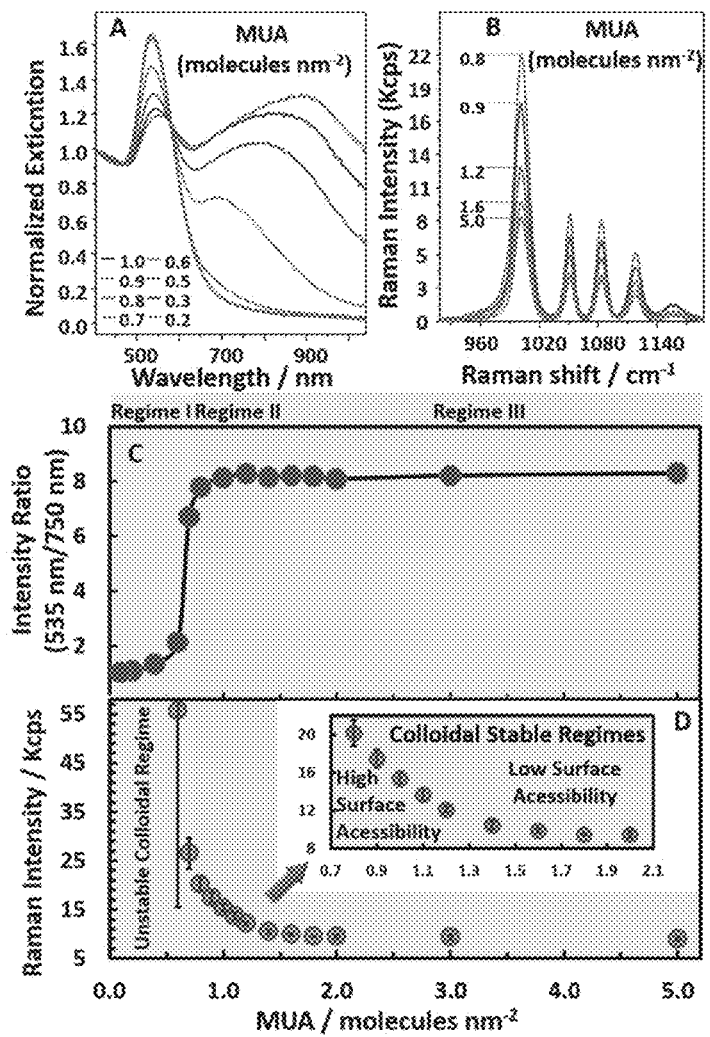
FIG. 2: (A) Extinction spectra of the Au@MUA/MPy nanoparticles with different amount of MUA (molecules $nm^{-2}$). MPy was always added in a large excess to guarantee the full coating of the nanoparticles. Below 0.8 MUA molecules $nm^{-2}$, it is possible to recognize an unstable colloidal regime (nanoparticles start aggregating). (B) SERS spectra of Au@MUA/MPy nanoparticles with different amount of MUA (molecules $nm^{-2}$). (C) Intensity ratio between the Abs at 535 and the Abs at 750 nm for Au@MUA/MPy nanoparticles as a function of different amount of MUA. (D) SERS intensity of Au@MUA/MPy nanoparticles as a function of different amount of MUA.
Figure 8:
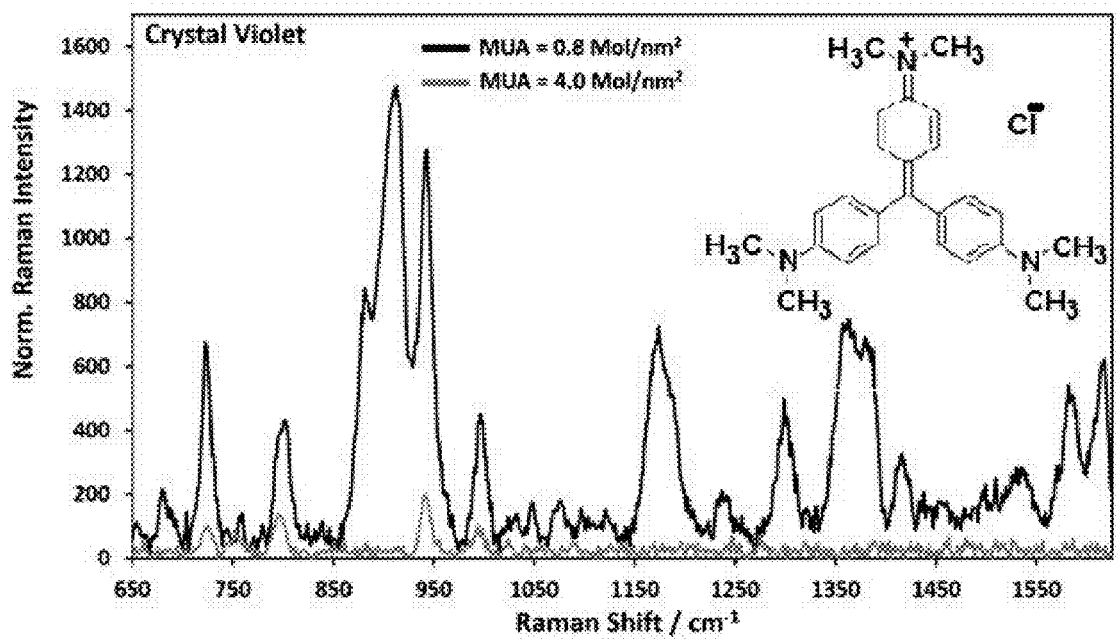
FIG. 8: Comparison of the SERS spectra of CV at two different MUA molecules/nm$^2$ (0.8 black and 4 red). Showing that almost no signal is obtained when 4 molecules per nm$^2$ were used.

MUA has been reported to take up an area of 0.22 nm$^2$, corresponding to ca. 4.5 molecules nm$^{-2}$.[21] Therefore, experiments decreasing the amount of MUA were designed in between 5.0 to 0.1 molecules nm$^{-2}$. After waiting for MUA adsorption to reach its thermodynamic equilibrium (30 min), the MPy was added in a large excess (15 molecules nm$^{-2}$) to yield the corresponding Au@MUA/MPy nanoparticles. Aggregation of the colloidal system was monitored by UV-Vis-NIR spectroscopy (FIG. 2A) by comparing the absorption of the resulting solutions at 535 nm, associated with isolated Au@MUA nanoparticles, and that at 750 nm, attributed to plasmonic contributions of interacting particles indicative of aggregation (FIG. 2C). Concurrently, SERS was also monitored in the same samples to estimate the amount of adsorbed code (FIG. 2B). Between 5-0.8 MUA molecules nm$^{-2}$ (stable colloidal regime), the extinction spectra of Au@MUA/MPy exhibit the characteristic LSPRs of isolated spherical gold nanoparticles in suspension. At 0.7 molecules nm$^{-2}$, the appearance of a shoulder at ca. 700 nm is observed, indicating the significant formation of nanoparticle aggregates. Further decrease of the MUA surface coverage leads to a dramatic perturbation of the colloidal stability upon addition of the MPy, as clearly revealed by the dominant plasmonic contribution at longer wavelength. Therefore, the range of colloidal stability was identified between 5 to 0.8 MUA molecules nm$^{-2}$ range. Conversely, the SERS intensity of the ring breathing mode of MPy at 1001 cm$^{-1}$ (FIG. 2D) indicates the existence of three regimes. The first corresponds to the particle aggregation (below 0.8 MUA molecules nm$^{-2}$ range) and, as expected, shows a remarkably increase of the intensity due to the uncontrolled plasmon coupling (see standard deviation). The second, between 1.4-0.8 MUA molecules nm$^{-2}$, reveals a progressively decrease in the SERS intensity of MPy as the MUA content increases. In this regime, an increase in MUA surface coverage is directly reflected in the decrement of code adsorption onto the metal surface. In the third regime, 1.6-5 MUA molecules nm$^{-2}$, the SERS intensity remains constant as MUA forms a progressively full monolayer and only a fixed amount of MPy molecules can diffuse onto the nanoparticles surfaces. Notably, for small molecules such as MPy, SERS intensity never decays to zero. This is because, differently to the crystalline arrangement of the densely packed films of alkanethiols on gold surfaces,[22] the coulomb repulsions between the negatively carboxilic groups of MUA limit the lateral interactions of the hydrophobic alkyl chains preventing the formation of a thick molecular packing on the surface.[23] Clearly, the accessibility to the metal surface in this particular regime is highly dependent on the chemical and geometrical properties of the SERS code. For instance, for MUA concentration of 4 molecules nm$^{-2}$ almost no SERS signals are observed for large molecular codes (see FIG. 8). Therefore 0.8 molecules nm$^{-2}$ was identified as the optimum MUA concentration for the production of our SERS-encoded gold nanoparticles, preventing aggregation and maximizing the SERS signal.

Figure 3:
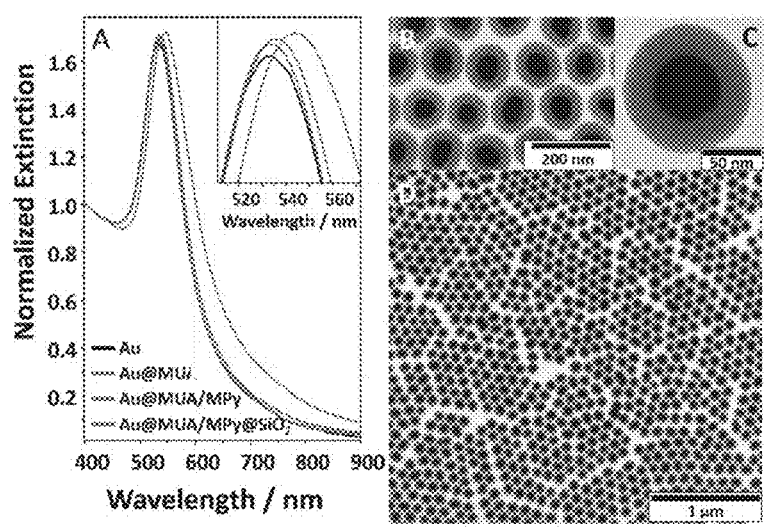
FIG. 3: (A) Extinction spectra of the Au particles during all the steps involved in the formation of the encoded nanoparticles. Showing that particles do not aggregate during process. (B, C and D) Representative TEM images at different magnifications of the MPy SERS-encoded nanoparticles.
Figure 9:
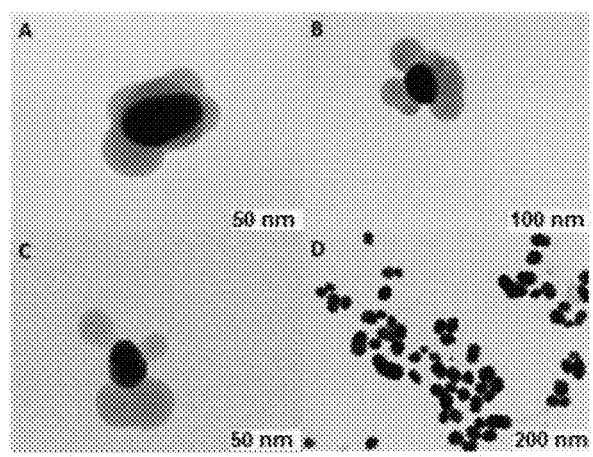
FIG. 9: (A, B, and C) TEM images showing the results of encoding nanoparticles at MUA concentrations below 0.8 molecules nm$^{-2}$ (0.7, 0.6 and 0.5 respectively). (D) TEM image showing the uncontrolled aggregation of the particles below 0.7 molecules nm$^{-2}$.

Finally, to ensure stability for long periods of time, protect both the Raman code and the plasmonic core, and generate a readably functionalizable external surface, the Au@MUA-MPy nanoparticles were encapsulated in a silica matrix. Silica coating was performed using a modification of the Stöber method[24] by exploiting the ability of ligands with terminal carboxylic acid, such as MUA, to induce the silica growth.[25] To this end, appropriate amounts of ethanol and NH$_4$OH were added to the Au@MUA/MPy aqueous suspension to maintain the adequate pH of the solution and provide the correct EtOH/H$_2$O molar ratio (1.84) for the Stöber process. Then, TEOS was added to initiate the silica growth. The solution was allowed to react for 14 h at room temperature before submitting it to several washing cycles (FIGS. 3B-D illustrates characteristic TEM images of Au@MUA/MPy@SiO$_2$ nanoparticles). FIG. 3A recollects the extinction spectra of the colloidal suspension after each fabrication step. As it can be seen, the shift of the LSPRs of individual nanoparticles clearly reflects the changes in the refractive index associated with each functionalization step (FIG. 3A, inset). Firstly, the sub-monolayer deposition of MUA induces minimal changes in the plasmon maxima, then full coating with MPy results in a ca. 3 nm shift and, finally, the growth of a thick silica layer is responsible for the large displacement up to 545 nm. Importantly, the extinction spectra do not reveal any significant broadening of the LSPR indicating that the nanoparticles preserve their colloidal stability during the whole process with no appreciable formation of aggregates. It is worth noting that, independently of the SERS encoding process and the related colloidal stability, homogeneous silica coatings can be only achieved for MUA concentration above 0.7 molecules $nm^{-2}$ (see FIG. 9).

Figure 4:
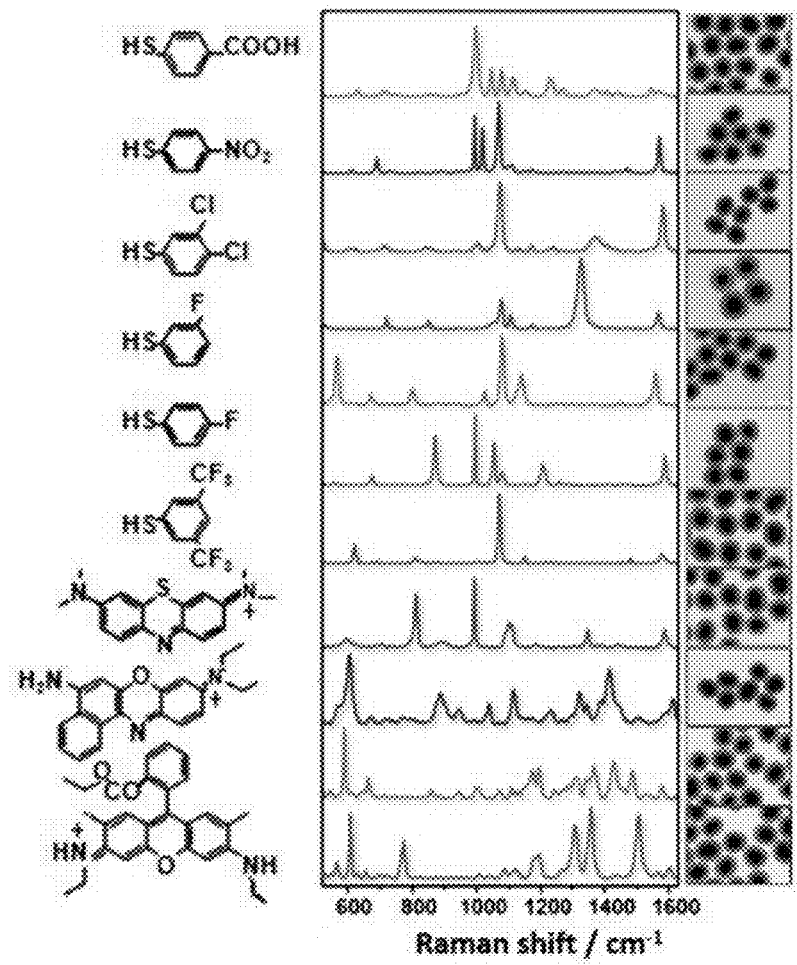
FIG. 4: SERS spectra of ten representative SERS-encoded nanoparticles. From the top to the bottom: 2-mercaptopyridine (MPy); benzenethiol (BT); mercaptobenzoic acid (MBA); 4-nitrobenzenethiol (4-NBT); 3,4-dicholorobenzenethiol (DBT), 3-fluorothiophenol (3-FTP); 4-fluorothiophenol (4-FTP); 3-5-bis(trifluoromethyl)benzenethiol (3-FMBT); methylene blue (MB); nile blue A (NBA); and rhodamine 6G (R6G).
Figure 10:
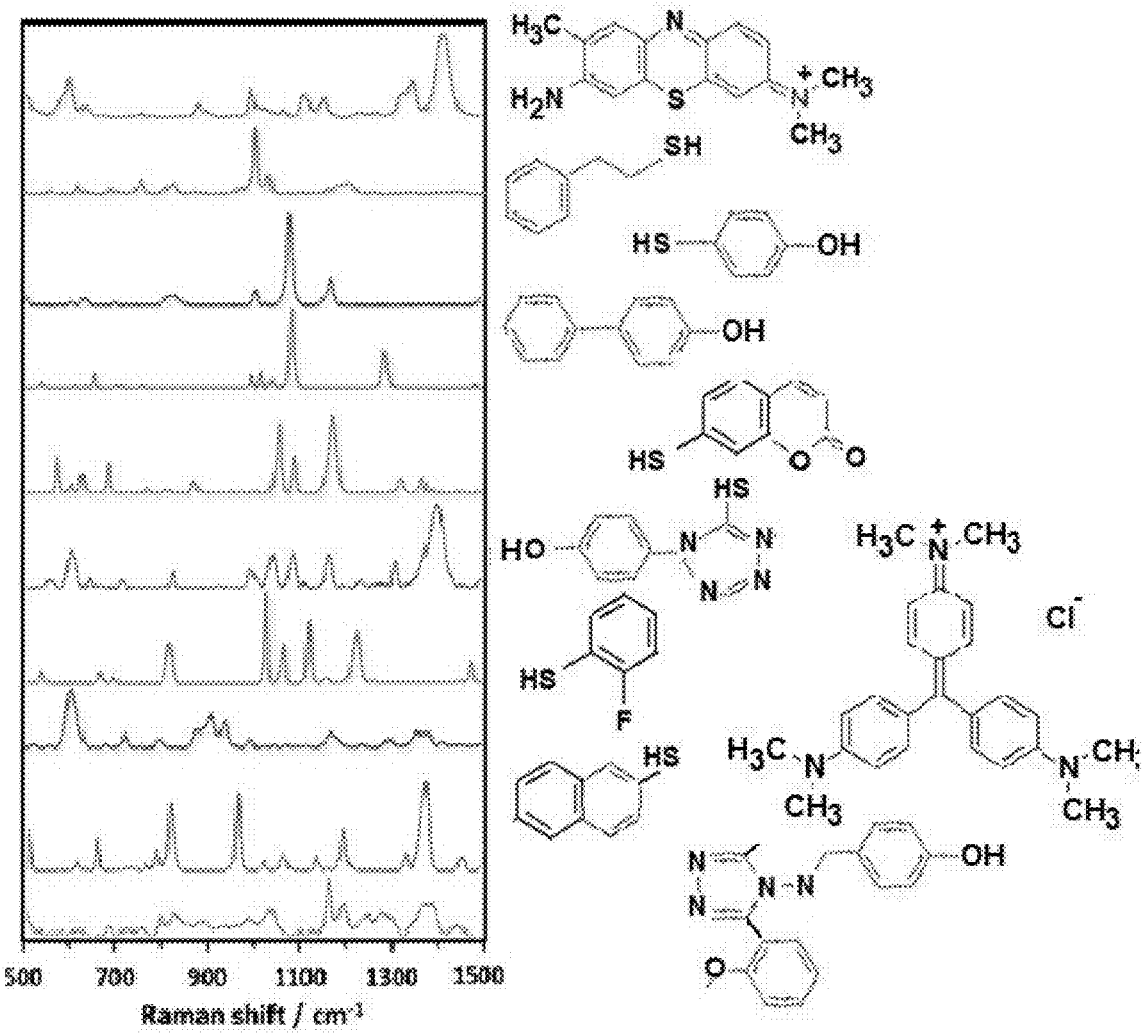
FIG. 10: SERS spectra of 20 representative SERS-encoded nanoparticles. Left column: Toluidine Blue O, 2-Phenylethanethiol, 4-Mercaptophenol, Biphenyl-4-thiol, 7-Mercapto-4-methylcoumarin, 4-Hydroxyphenyl)-1H-tetrazole-5-thiol, 2-Fluorothiophenol, Crystal Violet, 2-Naphthalenethiol, 4-(((3-Mercapto-5-(2-methoxyphenyl)-4H-1,2,4-triazol-4-yl)imino)methyl)phenol. Right column: (2-Trifluoromethyl)benzenethiol, 4-Aminothiophenol, 1-Naphthalenethiol, 1,1',4,1"-Terphenyl-4-Thiol, Biphenyl-4,4'-dithiol, Thiosalicylic acid, 4-(((3-Mercapto-5-(2-pyridinyl)-4H-1,2,4-triazol-4-yl)imino)methyl)-1,2-benzenediol, 4-(((3-Mercapto-5-(2-pyridinyl)-4H-1,2,4-triazol-4-yl)imino)methyl)benzoic, 2,3,4,6-Tetrafluorobenzenethiol, (5-(4-Methoxyphenyl)-1,3,4-oxidazole-2-thiol).
Figure 11:
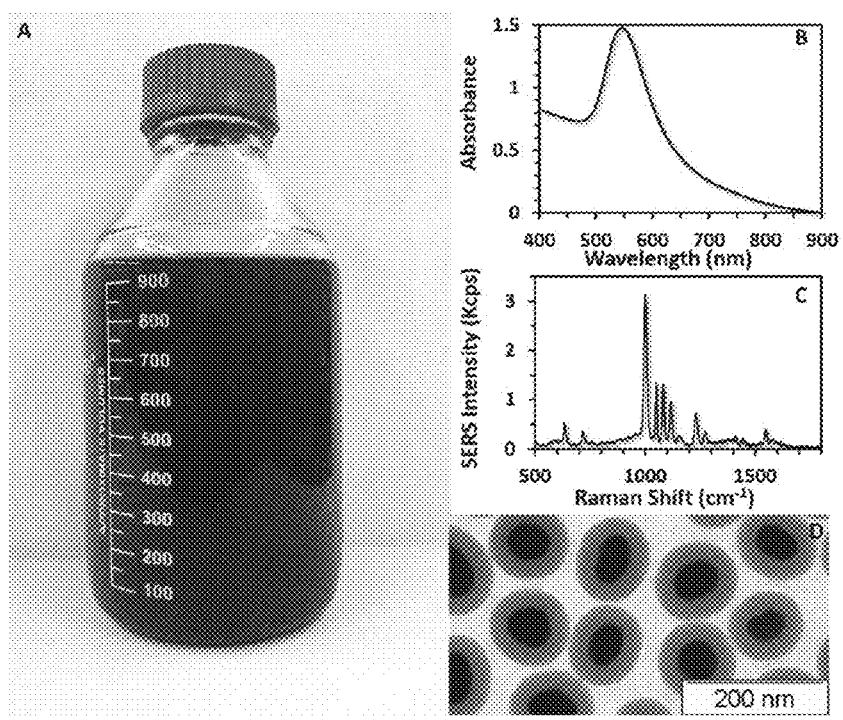
FIG. 11: (A) Photography of the one-pot synthesis of a liter batch of MPy encoded nanoparticles. (B) UV-Vis, (C) SERS spectra, and (D) TEM image of the encoded nanoparticles.

The described protocol was successfully extended to a large set of different codes, including thiolated and non-thiolated aromatic small molecules and dyes (phenothiazines, rhodamines, oxazines, triarylmethanes, tri- and tetrazoles, etc.), proving the universal applicability of this synthetic strategy. FIG. 4 shows the SERS signatures and TEM images of 11 representative SERS-encoded nanoparticles, whereas another 20 codes are reported in the supporting information (FIG. 10). Notably, the one-pot synthetic method has been successfully employed in the fabrication of larger volumes of SERS-encoded nanoparticles (at the liter regime, FIG. 11) without impacting the final characteristics of the substrate, which clearly demonstrates the scalability of the process.

In order to evaluate the optical efficiency of our protocol, we compared the SERS intensities provided by seven of our SERS-encoded nanoparticles with those yielded by their analogous counterparts fabricated (when possible) with the most common polymer-based procedures used in the literature: PVP and thiolated PEG approaches.[19, 26] Both polymer-based strategies relay in providing the required stability to the Au particles during the codification step. To this end, the reported recipes[19, 26] were followed and optimized in order to achieve the highest possible SERS signal. When PVP was used, citrate-stabilized Au nanoparticles were first produced and the subsequently transferred to EtOH using PVP. Prior to the code addition, the particles were extensively washed to remove as much as possible the PVP from the surface of the particles while preserving the colloidal stability. These washing cycles are critical to maximize the adsorption of the code onto the metallic surface.

Figure 5:
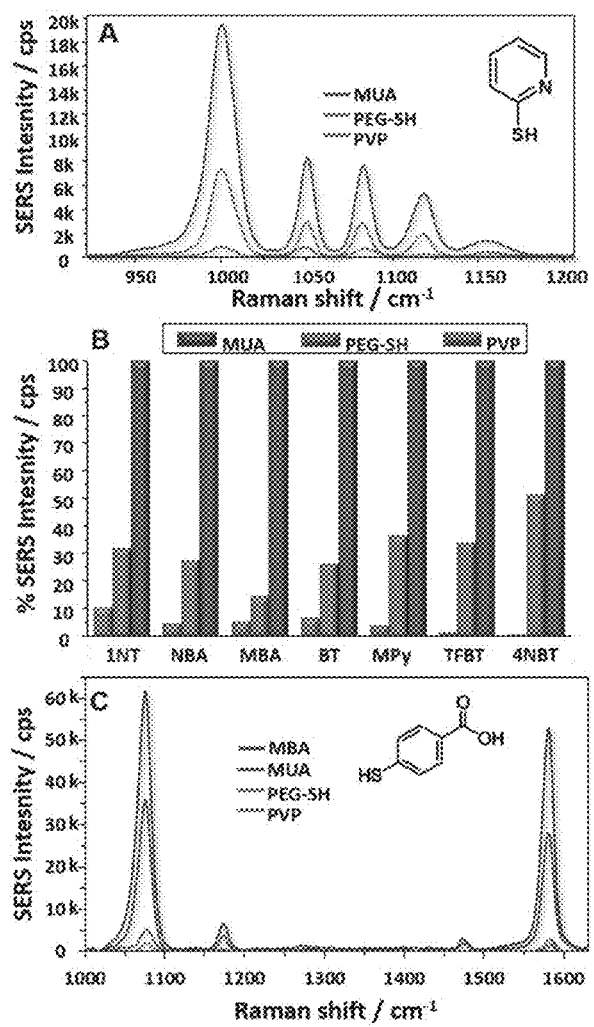
FIG. 5: (A) SERS spectra in the 900-1210 cm-1 region of comparison of MPy encoded nanoparticles prepared using the PVP, PEG-SH and MUA approaches. (B) Relation of the SERS efficiency of the three synthetic methods for 1NT, NBA, MBA, TB, MPy, TFBT, and 4NBT encoded nanoparticles (the corresponding SERS spectra are shown in FIG. 6). (C) SERS spectra in the 1000-1630 cm-1 region of comparison of MBA encoded nanoparticles prepared using a full monolayer of MBA (Purple) and combinations with the different stabilizing agents used: MUA+MBA (Green), PEG-SH+MBA (red), and PVP+MBA (Blue).
Figure 12:
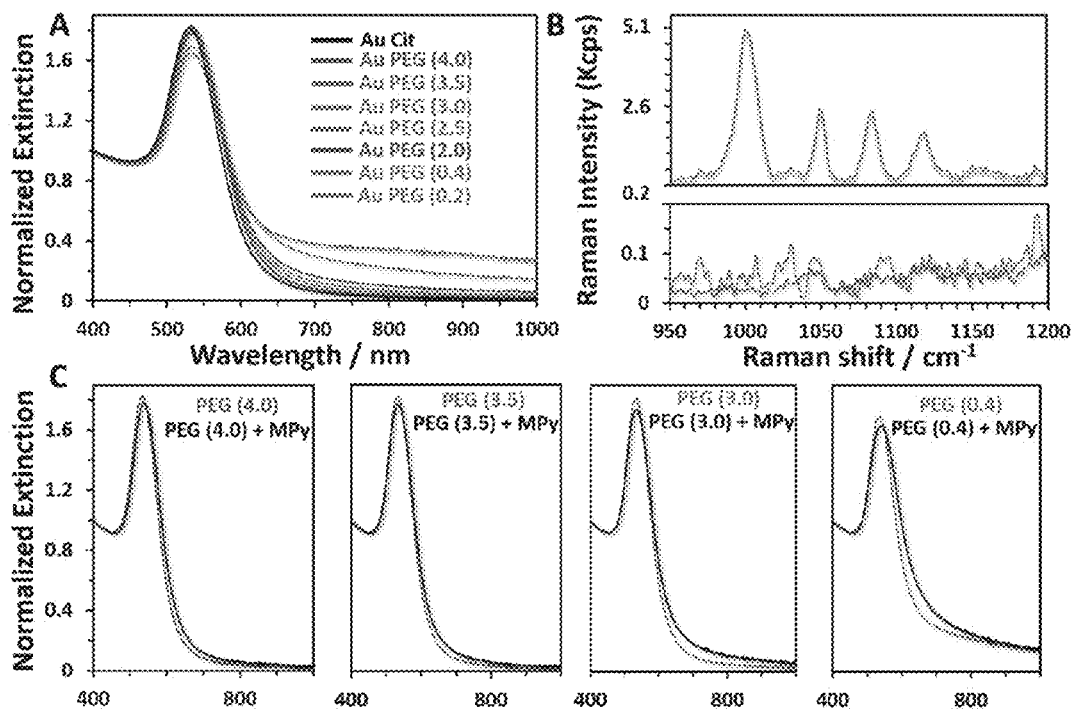
FIG. 12: (A) SERS spectra comparison of encoded nanoparticles prepared using the PVP, PEG-SH and MUA approaches (blue, red, and green respectively) of MBA, 4NBT, NBA, TB, TFBT, and 1NT.
Figure 13:
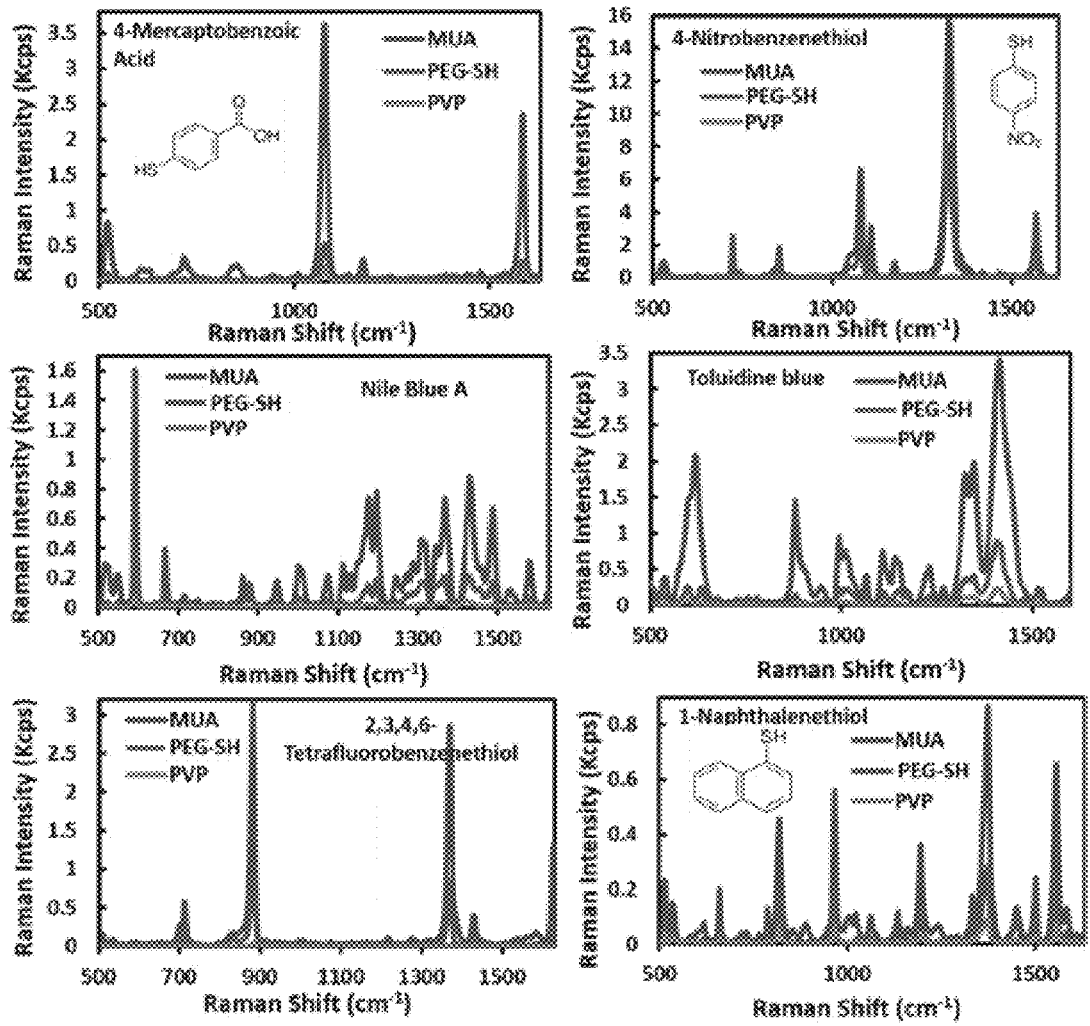
FIG. 13: SERS spectra comparison of encoded nanoparticles prepared using the PVP, PEG-SH and MUA approaches (blue, red, and green respectively) of MBA, 4NBT, NBA, TB, TFBT, and 1NT.
Figure 13:
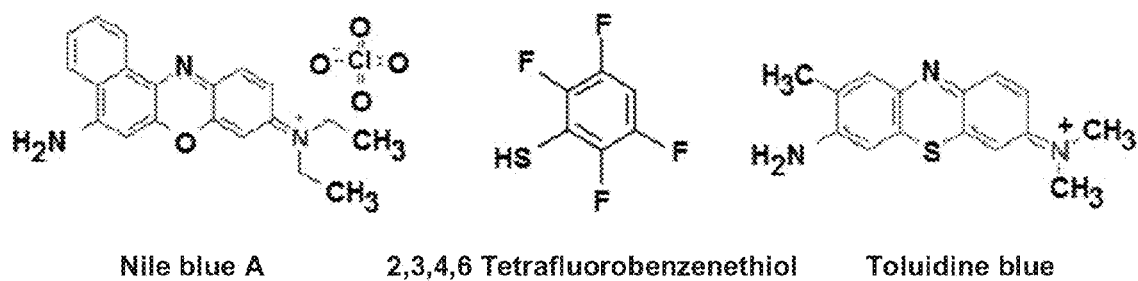

In the case of thiolated-PEG, it has been previously shown that the polymeric layer significantly hinders the diffusion of molecules onto the metal surface.[26] Consequently, due to the very limited number of Raman molecules capable to bind PEG-coated nanoparticles, the use of the corresponding Au@PEG@code particles is largely limited to surface-enhanced resonant Raman conditions (SERRS), when the electronic excitation of the dye is in resonance with the laser beam.[19,27] Identical limitation appears if the codification step is performed prior to the PEG coating (Au@code@PEG)[28] because, in this case, except for few fortunate cases of "nanoparticle stabilizing" Raman codes such as MBA, the number of molecules per $nm^2$ that can be adsorbed onto the metal without perturbing the colloidal stability is very small. We therefore first tried to improve the Raman label accessibility to the metal surface (i.e. increasing the number of code molecules per nanoparticle) by progressively lowering the PEG-SH concentration from 4 molecules $nm^{-2}$, as reported in the literature,[19] to 0.2. However, nanoparticle aggregation is already observed at a polymer concentration less than 3.5 molecules $nm^{-2}$ even prior to the addition of the excess of MPy (FIG. 12). Moreover, no distinguishable SERS signals were recorded upon functionalization of the PEG-coated gold nanoparticles with the excess of MPy unless in the presence of colloidal aggregation (FIG. 12). Discarded the possibility to increase the MPy surface coverage by decreasing the PEG-SH concentration, we pursue a different strategy.[26,27] In this case, CTAB-stabilized Au nanoparticles of similar size were prepared instead of citrate-capped colloids. The surfactant double layer offers an effective stabilizing shell preventing the nanoparticle aggregation when the colloids are exposed to less PEG amount (corresponding to 1.8 molecules $nm^{-2}$ in our optimized experimental conditions). The resultant PEG/CTAB-stabilized nanoparticles can then be submitted to, firstly, several washing cycles to remove excess of surfactant and, secondly, to the excess of MPy in the codification step without impacting the colloidal stability. This optimized protocol allows us to synthesize SERS-encoded nanoparticles with much higher SERS efficiency, generally larger than that observed for the PVP approach, but still significantly lower than that provided by the MUA-based method. (FIG. 5A and FIG. 13). Furthermore, it is important to stress that even when optimized, the combined CTAB/PEG approach retains intrinsic limitations and problems, such as the necessity of multiple cycles of centrifugation, separation and resuspension (which are often critical for the colloidal stability as well as represent a practical obstacle for their large scale production), the use of large amounts of the highly cytotoxic CTAB,[29] etc.

TABLE 1 below summarizes the SERS intensities obtained for the different synthetic methods using seven different Raman code:

|  | NBA | TB | 2MPy | 1NT | MBA | TH60 | 4NBT |
| --- | --- | --- | --- | --- | --- | --- | --- |
| PVP | 22.2 | 14.9 | 26.5 | 10 | 19.4 | 79 | 140 |
| PEG-SH | 3.6 | 3.8 | 2.7 | 3.1 | 7 | 2.9 | 2 |

Table 1. Surface accessibility enhancement of SERS intensity for MUA encoded nanoparticles for each code related to the PVP and PEG-SH respectively.

For all the investigated cases, the SERS intensity achieved with the MUA-based protocol was between 140 to 10 times higher than in the case of PVP, and from 10 to 2 times higher than in the case of thiolated-PEG. Such drastic differences from one Raman label to another can be ascribed to the different chemical nature and molecular size of the codes which clearly affect its ability to diffuse through the external polymeric layer and finally adsorb onto the metal surface.

As previously indicated, modification of the nanoparticle surface chemistry by adsorption of Raman labels normally results in a decrease of colloidal stability in suspension. However, in very few cases, the specific chemical nature of code molecule can still preserve such stability acting as a stabilizing agent. This is the case, for instance, of mercaptobenzoic acid (MBA). As for MUA, the carboxylic groups of MBA bound to the metal surface are oriented toward the bulk solution providing, at basic pH, the necessary electrostatic repulsion to avoid nanoparticle aggregation and, in the subsequent silica-coating step, promote the silica growth. As a result, this SERS-encoded nanoparticle can be synthesized at full MBA coverage with no need of external stabilizing agents. We therefore assess the SERS performance of MBA-encoded nanoparticles produced via our MUA synthetic method with respect to the same SERS tags obtained at full MBA coverage (i.e. zero MUA molecules $nm^{-2}$, maximum SERS efficiency). FIG. 5C shows the corresponding SERS spectra as well as those of the analogous SERS tags synthesized via PVP and thiolated-PEG methods. Notably, MUA functionalization results in a 42% loss with respect to the maximum SERS efficiency, which is much less than those observed for PVP (ca. 97% reduction) and thiolated-PEG (92% reduction) methods.

Experimental Conclusions of Examples

In summary, herein we describe a universal, reproducible independently of the chemical brand and batches, one-pot, inexpensive and scalable synthetic protocol for the fabrication of SERS-encoded nanoparticles. This method relies on the functionalization of plasmonic nanoparticles with a submonolayer of mercaptoundecanoic acid providing high colloidal stability during the codification process while allowing Raman labels to easily diffuse onto the metal. Furthermore, in a subsequent step, the carboxylic groups of MUA also act as functional sites promoting the silica growth on the outer shell of the nanoparticles.

This synthetic strategy has proven to be successfully applicable to every Raman code we tested (31 codes) and scalable up to two liters without affecting the final properties of the encoded structures. Finally, the SERS efficiency of the so-fabricated encoded nanoparticles has shown to be from 2 to 140 times higher than the corresponding SERS-tags prepared via the common polymer-based methods (PVP and thiolated-PEG).

REFERENCES

[1] a) A. Doerr, *Nat Meth* 2007, 4, 381; b) H. Fenniri, R. Alvarez-Puebla, *Nat. Chem. Biol.* 2007, 3, 247.
[2] R. Wilson, A. R. Cossins, D. G. Spiller, *Angew. Chem. Int. Ed.* 2006, 45, 6104.
[3] a) Y. Zhao, X. Zhao, J. Hu, M. Xu, W. Zhao, L. Sun, C. Zhu, H. Xu, Z. Gu, *Adv. Mater.* 2009, 21, 569; b) L. Rodriguez-Lorenzo, L. Fabris, R. A. Alvarez-Puebla, *Anal. Chim. Acta* 2012, 745, 10; c) F. Zheng, Y. Cheng, J. Wang, J. Lu, B. Zhang, Y. Zhao, Z. Gu, *Adv. Mater.* 2014, n/a.
[4] G. Shtengel, J. A. Galbraith, C. G. Galbraith, J. Lippincott-Schwartz, J. M. Gillette, S. Manley, R. Sougrat, C. M. Waterman, P. Kanchanawong, M. W. Davidson, R. D. Fetter, H. F. Hess, *Proc. Nat. Acad. Sci. USA* 2009, 106, 3125.
[5] a) K. Braeckmans, S. C. De Smedt, M. Leblans, R. Pauwels, J. Demeester, *Nat. Rev. Drug. Discov.* 2002, 1, 447; b) K. Braeckmans, S. C. De Smedt, *Nat. Mater.* 2010, 9, 697; c) K. Braeckmans, S. C. De Smedt, C. Roelant, M. Leblans, R. Pauwels, J. Demeester, *Nat. Mater.* 2003, 2, 169; d) K. D. Bake, D. R. Walt, Ann. Rev. Anal. Chem. 2008, 1, 515; e) W. E. Doering, M. E. Piotti, M. J. Natan, R. G. Freeman, *Adv. Mater.* 2007, 19, 3100; f) R. G. Freeman, P. A. Raju, S. M. Norton, I. D. Walton, P. C. Smith, L. He, M. J. Natan, M. Y. Sha, S. G. Penn, *Method Mol. Biol.* 2005, 303, 73; g) S. R. Nicewarner-Pena, R. G. Freeman, B. D. Reiss, L. He, D. J. Pena, I. D. Walton, R. Cromer, C. D. Keating, M. J. Natan, *Science* 2001, 294, 137; h) M. Y. Sha, I. D. Walton, S. M. Norton, M. Taylor, M. Yamanaka, M. J. Natan, C. Xu, S. Drmanac, S. Huang, A. Borcherding, R. Drmanac, S. G. Penn, *Anal. Bioanal. Chem.* 2006, 384, 658.
[6] a) F. Cunin, T. A. Schmedake, J. R. Link, Y. Y. Li, J. Koh, S. N. Bhatia, M. J. Sailor, *Nat Mater* 2002, 1, 39; b) N. H. Finkel, X. Lou, C. Wang, L. He, *Anal. Chem.* 2004, 76, 352 A; c) D. C. Pregibon, M. Toner, P. S. Doyle, *Science* 2007, 315, 1393.
[7] A. R. Vaino, K. D. Janda, *Proc. Nat. Acad. Sci. USA* 2000, 97, 7692.
[8] H. Fenniri, L. Ding, A. E. Ribbe, Y. Zyrianov, *J. Am. Chem. Soc.* 2001, 123, 8151.
[9] a) M. Bruchez, M. Moronne, P. Gin, S. Weiss, A. P. Alivisatos, *Science* 1998, 281, 2013; b) J. Raez, D. R. Blais, Y. Zhang, R. A. Alvarez-Puebla, J. P. Bravo-Vasquez, J. P. Pezacki, H. Fenniri, *Langmuir* 2007, 23, 6482; c) J. Lee, P. W. Bisso, R. L. Srinivas, J. J. Kim, A. J. Swiston, P. S. Doyle, *Nat. Mater.* 2014, 13, 524.
[10] M. Sanles-Sobrido, W. Exner, L. Rodriguez-Lorenzo, B. Rodriguez-Gonzalez, M. A. Correa-Duarte, R. A. Alvarez-Puebla, L. M. Liz-Marzan, *J. Am. Chem. Soc.* 2009, 131, 2699.
[11] G. Goddard, L. O. Brown, R. Habbersett, C. I. Brady, J. C. Martin, S. W. Graves, J. P. Freyer, S. K. Doorn, *J. Am. Chem. Soc.* 2010, 132, 6081.
[12] a) M. Howarth, W. Liu, S. Puthenveetil, Y. Zheng, L. F. Marshall, M. M. Schmidt, K. D. Wittrup, M. G. Bawendi, A. Y. Ting, *Nat. Meth.* 2008, 5, 397; b) X. Qian, X.-H. Peng, D. O. Ansari, Q. Yin-Goen, G. Z. Chen, D. M. Shin, L. Yang, A. N. Young, M. D. Wang, S. Nie, *Nat Biotech* 2008, 26, 83; c) A. Serge, N. Bertaux, H. Rigneault, D. Marguet, *Nat. Meth.* 2008, 5, 687.
[13] P. Rivera_Gil, C. Vazquez-Vazquez, V. Giannini, M. P. Callao, W. J. Parak, M. A. Correa-Duarte, R. A. Alvarez-Puebla, *Angew. Chem. Int. Ed.* 2013, 52, 13694.
[14] a) J. Song, J. Zhou, H. Duan, *J. Am. Chem. Soc.* 2012, 134, 13458; b) N. Pazos-Perez, C. S. Wagner, J. M. Romo-Herrera, L. M. Liz-Marzán, F. J. Garcia de Abajo, A. Wittemann, A. Fery, R. A. Alvarez-Puebla, *Angew. Chem. Int. Ed.* 2012, 51, 12688.
[15] a) A. Guerrero-Martinez, J. Pérez-Juste, L. M. Liz-Marzán, *Adv. Mater.* 2010, 22, 1182; b) R. Jiang, B. Li, C. Fang, J. Wang, *Adv. Mater.* 2014, 26, 5274.
[16] S. Liu, M.-Y. Han, *Chem. Asian J.* 2010, 5, 36.
[17] a) M. Alba, N. Pazos-Perez, B. Vaz, P. Formentin, M. Tebbe, M. A. Correa-Duarte, P. Granero, J. Ferré-Borrull, R. Alvarez, J. Pallares, A. Fery, A. R. de Lera, L. F. Marsal, R. A. Alvarez-Puebla, *Angew. Chem. Int. Ed.* 2013, 52, 6459; b) R. A. Alvarez-Puebla, A. Agarwal, P. Manna, B. P. Khanal, P. Aldeanueva-Potel, E. Carbó-Argibay, N. Pazos-Pérez, L. Vigderman, E. R. Zubarev, N. A. Kotov, L. M. Liz-Marzán, *Proc. Nat. Acad. Sci. USA* 2011, 108, 8157.
[18] a) X. Su, J. Zhang, L. Sun, T. W. Koo, S. Chan, N. Sundararajan, M. Yamakawa, A. A. Berlin, *Nano Lett.* 2005, 5, 49; b) L. Sun, K.-B. Sung, C. Dentinger, B. Lutz, L. Nguyen, J. Zhang, H. Qin, M. Yamakawa, M. Cao, Y. Lu, A. J. Chmura, J. Zhu, X. Su, A. A. Berlin, S. Chan, B. Knudsen, *Nano Lett.* 2007, 7, 351.
[19] C. Fernández-López, C. Mateo-Mateo, R. A. Álvarez-Puebla, J. Pérez-Juste, I. Pastoriza-Santos, L. M. Liz-Marzán, *Langmuir* 2009, 25, 13894.
[20] a) P. J. G. Goulet, N. P. W. Pieczonka, R. F. Aroca, *Anal. Chem.* 2003, 75, 1918; b) P. J. G. Goulet, R. F. Aroca, *Anal. Chem.* 2007, 79, 2728.
[21] H. Hiramatsu, F. E. Osterloh, *Langmuir* 2003, 19, 7003.
[22] M. A. Bryant, J. E. Pemberton, *J. Am. Chem. Soc.* 1991, 113, 8284.
[23] a) L. Guerrini, I. Izquierdo-Lorenzo, J. V. Garcia-Ramos, C. Domingo, S. Sanchez-Cortes, *Phys. Chem. Chem. Phys.* 2009, 11, 7363; b) L. Guerrini, I. Izquierdo-Lorenzo, R. Rodriguez-Oliveros, J. A. Sanchez-Gil, S. Sanchez-Cortes, J. V. Garcia-Ramos, C. Domingo, *Plasmonics* 2010, 5, 273.
[24] W. Stöber, A. Fink, E. Bohn, *J. Colloid Interface Sci.* 1968, 26, 62.

[25] a) A. F. Wallace, J. J. DeYoreo, P. M. Dove, *J. Am. Chem. Soc.* 2009, 131, 5244; b) T. Chen, G. Chen, S. Xing, T. Wu, H. Chen, *Chem. Mater.* 2010, 22, 3826; c) C. Xue, X. Chen, S. J. Hurst, C. A. Mirkin, *Adv. Mater.* 2007, 19, 4071; d) Y. J. Wong, L. Zhu, W. S. Teo, Y. W. Tan, Y. Yang, C. Wang, H. Chen, *J. Am. Chem. Soc.* 2011, 133, 11422; e) M. Rycenga, M. R. Langille, M. L. Personick, T. Ozel, C. A. Mirkin, *Nano Lett.* 2012, 12, 6218.

[26] L. Rodriguez-Lorenzo, Z. Krpetic, S. Barbosa, R. A. Alvarez-Puebla, L. M. Liz-Marzan, I. A. Prior, M. Brust, *Integ. Biol.* 2011, 3, 922.

[27] P. Šimáková, J. Gautier, M. Procházka, K. Hervé-Aubert, I. Chourpa, *J. Phys. Chem. C* 2014, 118, 7690.

[28] X. M. Qian, X. H. Peng, D. O. Ansari, Q. Yin-Goen, G. Z. Chen, D. M. Shin, L. Yang, A. N. Young, M. D. Wang, S. M. Nie, *Nat. Biotechnol.* 2008, 26, 83.

[29] C. J. Murphy, A. M. Gole, J. W. Stone, P. N. Sisco, A. M. Alkilany, E. C. Goldsmith, S. C. Baxter, *Acc. Chem. Res.* 2008, 41, 1721.

[30] N. Pazos-Perez, F. J. Garcia de Abajo, A. Fery, R. A. Alvarez-Puebla, *Langmuir* 2012, 28, 8909.

The invention claimed is:

1. A method for synthesizing encapsulated SERS encoded nanoparticles comprising the following steps:
   a) providing an aqueous suspension of metal nanoparticles;
   b) adding acid to the suspension to yield MUA-stabilized nanoparticles without forming a complete monolayer;
   c) adding a SERS encoding molecule to the suspension selected from molecules that has a functional group with high affinity to the metal surfaces as thiols, amines or cyanides; and
   d) encapsulating the SERS encoded nanoparticles in a silica matrix.

2. The method according to claim 1, wherein the suspension of metal nanoparticles is a suspension of nanoparticles of gold, silver, copper, aluminum, their alloys with themselves or their alloys with others.

3. The method according to claim 1, wherein step b) is carried out by adding mercaptoundecanoic acid to the suspension to yield MUA-stabilized nanoparticles.

4. The method according to claim 1, wherein step b) is carried out by adding a solution containing $NH_4OH$ and MUA rapidly and under vigorous stirring to the suspension of metal nanoparticles.

5. The method according to claim 1, wherein the suspension of metal nanoparticles is a suspension of citrate-capped spherical gold nanoparticles that is produced by adding an aqueous solution of $HAuCl_4$ into a boiling aqueous solution of sodium citrate under vigorous stirring, and then maintaining the heating and stirring at appropriate levels until the solvent is at least partially evaporated.

6. The method according to claim 1, wherein step c) is carried out by adding a solution containing EtOH and $NH_4OH$ to the suspension of MUA-stabilized nanoparticles and then adding thereto a solution containing the selected SERS encoding molecule.

7. The method of claim 6, wherein the addition of the solution containing EtOH and $NH_4OH$ to the suspension of MUA-stabilized nanoparticles is carried out rapidly and under vigorous stirring.

8. The method according to claim 1, wherein the solution containing the SERS encoding molecule is added to the suspension of MUA-stabilized nanoparticles under strong magnetic stirring and in a large excess of molecules per $nm^2$ with respect to the MUA-stabilized nanoparticles.

9. The method according to claim 1, wherein the SERS encoding molecule is selected from the group consisting of: 2-mercaptopyridine; benzenethiol; mercaptobenzoic acid; 4-nitrobenzenethiol; 3,4-dicholorobenzenethiol, 3-fluorothiophenol; 4-fluorothiophenol; 3-5-bis(trifluoromethyl)benzenethiol; methylene blue; nile blue A; rhodamine 6G; Toluidine Blue O, 2-Phenylethanethiol, 4-Mercaptophenol, Biphenyl-4-thiol, 7-Mercapto-4-methylcoumarin, 4-Hydroxyphenyl)-1H-tetrazole-5-thiol, 2-Fluorothiophenol, Crystal Violet, 2-Naphthalenethiol, 4-(((3-Mercapto-5-(2-methoxyphenyl)-4H-1,2,4-triazol-4-yl)imino)methyl)phenol, (2-Trifluoromethyl)benzenethiol, 4-Aminothiophenol, 1-Naphthalenethiol, 1,1',4,1''-Terphenyl-4-Thiol, Biphenyl-4,4'-dithiol, Thiosalicylic acid, 4-(((3-Mercapto-5-(2-pyridinyl)-4H-1,2,4-triazol-4-yl)imino)methyl)-1,2-benzenediol, 4-(((3-Mercapto-5-(2-pyridinyl)-4H-1,2,4-triazol-4-yl)imino)methyl)benzoic, 2,3,4,6-Tetrafluorobenzenethiol, and (5-(4-Methoxyphenyl)-1,3,4-oxidazole-2-thiol).

10. The method according to claim 9, wherein the SERS encoding molecule is 2-mercaptopyridine.

11. The method according to claim 1, wherein the encapsulation of the SERS encoded nanoparticles in a silica matrix is carried out by adding to the dispersion of SERS encoded nanoparticles appropriate amounts of ethanol and $NH_4OH$ to provide an $EtOH/H_2O$ molar ratio between 0.2 and 5, and then adding tetraethyl orthosilicate to initiate the silica growth.

12. The method of claim 11, wherein the solution is thereafter allowed to react between 1 h and 24 h at room temperature and then submitted to several washing cycles.

\* \* \* \* \*